United States Patent
Sumanaweera et al.

(10) Patent No.: US 6,293,914 B1
(45) Date of Patent: Sep. 25, 2001

(54) ULTRASONIC SYSTEM AND METHOD FOR MEASUREMENT OF FLUID FLOW

(75) Inventors: Thilaka S. Sumanaweera, San Jose; Patrick J. Phillips, Sunnyvale, both of CA (US)

(73) Assignee: Acuson Corporation, Mountain View, CA (US)

(*) Notice: Subject to any disclaimer, the term of this patent is extended or adjusted under 35 U.S.C. 154(b) by 0 days.

(21) Appl. No.: 09/144,587

(22) Filed: Aug. 31, 1998

(51) Int. Cl.$^7$ .................................................. A61B 8/00
(52) U.S. Cl. ............................ 600/465; 600/466; 600/443
(58) Field of Search .................................... 600/454, 455, 600/441, 437, 456, 443, 457, 453

(56) References Cited

U.S. PATENT DOCUMENTS

| | | |
|---|---|---|
| 4,067,236 | 1/1978 | Hottinger . |
| 4,103,679 | 8/1978 | Aronson . |
| 4,142,412 | 3/1979 | McLeod et al. . |
| 4,265,126 | 5/1981 | Papadofrangakis et al. . |
| 4,373,533 | 2/1983 | Iinuma . |
| 4,493,216 | 1/1985 | Hassler . |
| 4,790,322 | 12/1988 | Iinuma . |
| 5,515,857 | 5/1996 | Tsujino et al. . |
| 5,522,393 | 6/1996 | Phillips et al. . |
| 5,568,812 | 10/1996 | Murashita et al. . |
| 5,623,930 | 4/1997 | Wright et al. . |
| 5,624,382 | 4/1997 | Oppelt et al. . |
| 5,675,554 | 10/1997 | Cole et al. . |

FOREIGN PATENT DOCUMENTS

| | | |
|---|---|---|
| 0851241 A2 | 7/1998 | (EP) . |
| WO91/15999 | 10/1991 | (WO) . |

OTHER PUBLICATIONS

Fei, Ding–Yu, et al. "Angle Independent Doppler Color Imaging: Determination of Accuracy and a Method of Display" *Ultrasound in Medicine and Biology (1994)*, vol. 20, No. 2, pp. 147–155, published in US.

Hottinger, CF and JD Meindl. "Blood Flow Measurement Using The Attenuation–Compensated Volume Flowmeter" *Ultrasonic Imaging* (1979) vol. 1, No. 1, pp. 1–15, published in US.

Phillips, PJ et al. "Feasibility Study for a Two–Dimensional Diagnostic Ultrasound Velocity Mapping System" *Ultrasound in Medicine and Biology* (1995) vol. 21, No. 2, pp. 217–229, published in US.

Tsujino, H. et al. "Quantitative Measurement of Volume Flow Rate (Cardiac Output) by the Multibeam Doppler Method" *Journal of the American Society of Echocardiography*, (Sep.–Oct. 1995), vol. 8, No. 5, pp. 621–630, published in US.

*Primary Examiner*—Marvin M. Lateef
*Assistant Examiner*—Maulin Patel
(74) *Attorney, Agent, or Firm*—Craig A. Summerfield; Brinks Hofer Gilson & Lione (57) ABSTRACT

A system and methods for measuring the volume flow of fluid in an enclosed structure with an ultrasound system is provided. Manual designation of flow angles and areas may not be necessary. Velocities along two or more different scan lines in a first scan plane are obtained to determine an angle of flow within the enclosed structure. A Doppler spectrum parameter is measured from a transmission in a second scan plane substantially perpendicular to the first scan plane. Volume flow is calculated from the flow angle and the parameter. The scan planes are associated with rotating a linear array transducer or holding a multi-dimensional transducer in place. A C-scan method with a linear transducer may also be used.

31 Claims, 6 Drawing Sheets

I BEAM

FIG. 6(b)

T BEAM

FIG. 6(c)

+ BEAM

AZIMUTHAL VIEW

ULTRASONIC SYSTEM AND METHOD FOR MEASUREMENT OF FLUID FLOW

BACKGROUND OF THE INVENTION

This invention relates in general to ultrasound systems, and in particular to an ultrasound system for measuring fluid volume flow.

Volume flow measurements may be important for various medical diagnosis. Volume flow indicates blockage in blood vessels and the performance of diseased or transplanted organs. For example, changes in the blood flow out of a kidney over time may be determined. Other examples of clinical application of volume flow measurements include: blood flow through shunts, blood flow to or from transplanted or diseased organs, umbilical cord and uterine artery flow, flow through various arteries and vessels, the blood flow in the brachial artery before and after artificially induced ischemia, flow through mitral aortic tricuspid and pulmonic valves, and others.

Ultrasound systems have been used to estimate volume flow. For example, a mean velocity estimate for a small sample volume inside a vessel is obtained from spectral Doppler information. An angle of flow is estimated from a user input angle. The user also manually outlines the vessel's cross section to obtain an estimate of area. The mean velocity, area and the appropriate trigonometric function of the Doppler angle are multiplied to obtain a flow estimate. However, the various manual tracings and estimations are laborious and prone to inaccuracies due to human error. Furthermore, obtaining the mean velocity from one sample volume may not accurately represent the true mean velocity across the entire vessel.

In another ultrasound technique for measuring volume flow, a high spatial resolution image is used to measure the flow profile across a vessel. The individual estimates of flow from each volume cell within a vessel are summed together to obtain the total volume flow. However, due to non-ideal ultrasound beam profiles, the information from one volume cell may duplicate, in part, another volume cell. Furthermore, this technique assumes that flow is parallel to the vessel or requires user estimation of the flow angle.

In yet another ultrasound technique to obtain volume flow, the velocity profile across a vessel is assumed to correspond to a particular function, such as a parabolic or plug profile. A single velocity estimate is obtained at the center of the vessel and used to estimate volume flow. The area of the vessel is calculated either manually or assumed to be circular. However, the area measurement is prone to human or estimation errors, and the actual flow profiles of fluids within a vessel may not match the parabolic or plug functions. Furthermore, as discussed above, the flow angle is manually entered, making the volume flow calculation laborious and error prone.

In yet another ultrasound technique for measuring volume flow, a cross section of a vessel located within a sample volume is insonified using a C-scan. See Hottinger U.S. Pat. No. 4,067,236. Therefore, ultrasound information is obtained from a plane parallel to the face of the transducer. In order to obtain the C-scan information, a fixed one or two-element transducer or a two-dimensional array transducer is used. The first moment of the C-scan information is calculated, eliminating the need to measure the area of the vessel. Measuring data in a plane parallel to the face of the transducer also eliminates the need to measure the flow direction. However, this technique does not accurately estimate volume flow in vessels that run parallel to the face of the transducer. Additionally, specialized transducers are required.

SUMMARY

The present systems and methods may avoid many of the problems of the prior art. The present invention is defined by the following claims, and nothing in this section should be taken as a limitation on those claims. By way of introduction, the preferred embodiment described below includes a system and method for measuring the volume flow of fluid in an enclosed structure with an ultrasound system. Velocities along two different scan lines in a first scan plane are obtained to determine an angle of flow within the enclosed structure. A Doppler spectrum parameter is measured from a transmission in a second scan plane substantially perpendicular to the first scan plane. Volume flow is calculated from the flow angle and the parameter. Some examples of the various aspects of this invention are summarized below.

According to a first embodiment, a first area of the enclosed structure is uniformly insonified. A first parameter of a Doppler spectrum responsive to the insonification is measured. An angle associated with a direction of flow in the enclosed structure is obtained. Volume flow is determined as a function of the first parameter and the angle.

According to a second embodiment, a first parameter of a first Doppler spectrum is measured. First and second velocities associated with a first area and first and second scan lines at first and second angles, respectively, are also measured. A flow angle associated with flow in the enclosed structure is determined as a function of the first and second velocities and first and second angles. Volume flow is determined as a function of the first parameter and the flow angle.

According to a third embodiment, axial or azimuthal uniform insonification of a longitudinal section of the enclosed structure is used to determine volume flow. Scatterer calibration and normalization values associated with a cross-section of the enclosed structure are determined. The enclosed structure associated with a longitudinal cross-section is uniformly insonified either axially or azimuthally with a linear transducer. Volume flow is determined as a function of the scatter calibration and normalization values and the uniform insonification information.

Other embodiments are possible. Further aspects and advantages of the invention are discussed below in conjunction with the preferred embodiments.

DETAILED DESCRIPTION OF PREFERRED EMBODIMENTS

The volume flow, as calculated by the preferred embodiments discussed below, is graphically represented in FIG. 1. An enclosed structure 20, such as an artery, vessel, shunt, chamber, or other bodily structure, is shown. An arbitrary surface, S, 22 is shown inside the enclosed structure 20. An area element, dS, 24 is shown on the arbitrary surface 22. A vector 26 normal to the arbitrary surface 22 at the area element 24 is also shown. The velocity of scatters, u(r), at any location on the arbitrary surface 22, such as the area element 24, is shown as vectors 28. The cross-sectional area of the enclosed structure 20 perpendicular to the axis of the enclosed structure 20 is designated as $A_O$. The volume flow, Q, through the arbitrary surface 22 is given by:

$$Q = \int_S u(r) \cdot dS = A_0 u_0, \quad (1)$$

where $u_0$ is the mean velocity of scatters in a plane perpendicular to the axis of the enclosed structure 20, such as the plane defined by the smallest cross sectional area. Equation (1) is based on the assumption that there is no flow through the walls of the enclosed structure, and the flow passing through the arbitrary surface 22 exits through the cross sectional area $A_0$.

The preferred embodiments described below are designed to provide accurate measurements of volume flow. The measurements are based on the three-dimensional orientation of the vessel in relation to a transducer. Velocities associated with two scan lines at different angles in a first scan plane are obtained. A first moment (a parameter) of a Doppler spectrum associated with uniform insonification in a second scan plane are also obtained. The first scan plane is oriented to maximize the displayed area of the enclosed structure in the longitudinal view, and the second scan plane is oriented to minimize the width of the displayed area of the enclosed structure in the lateral view (the first scan plane is substantially perpendicular to the second scan plane). An angle of flow in the enclosed structure is determined as a function of the velocities. Volume flow is determined from the angle of flow and the parameter associated with the second scan plane.

A. Systems

Various ultrasound systems are capable of calculating the flow measurement as described above and detailed below. For example, an ultrasound system capable of obtaining Doppler velocity data along non-colinear scan lines, obtaining Doppler spectrum parameters and processing the data below may be used.

Figures 1, 2:
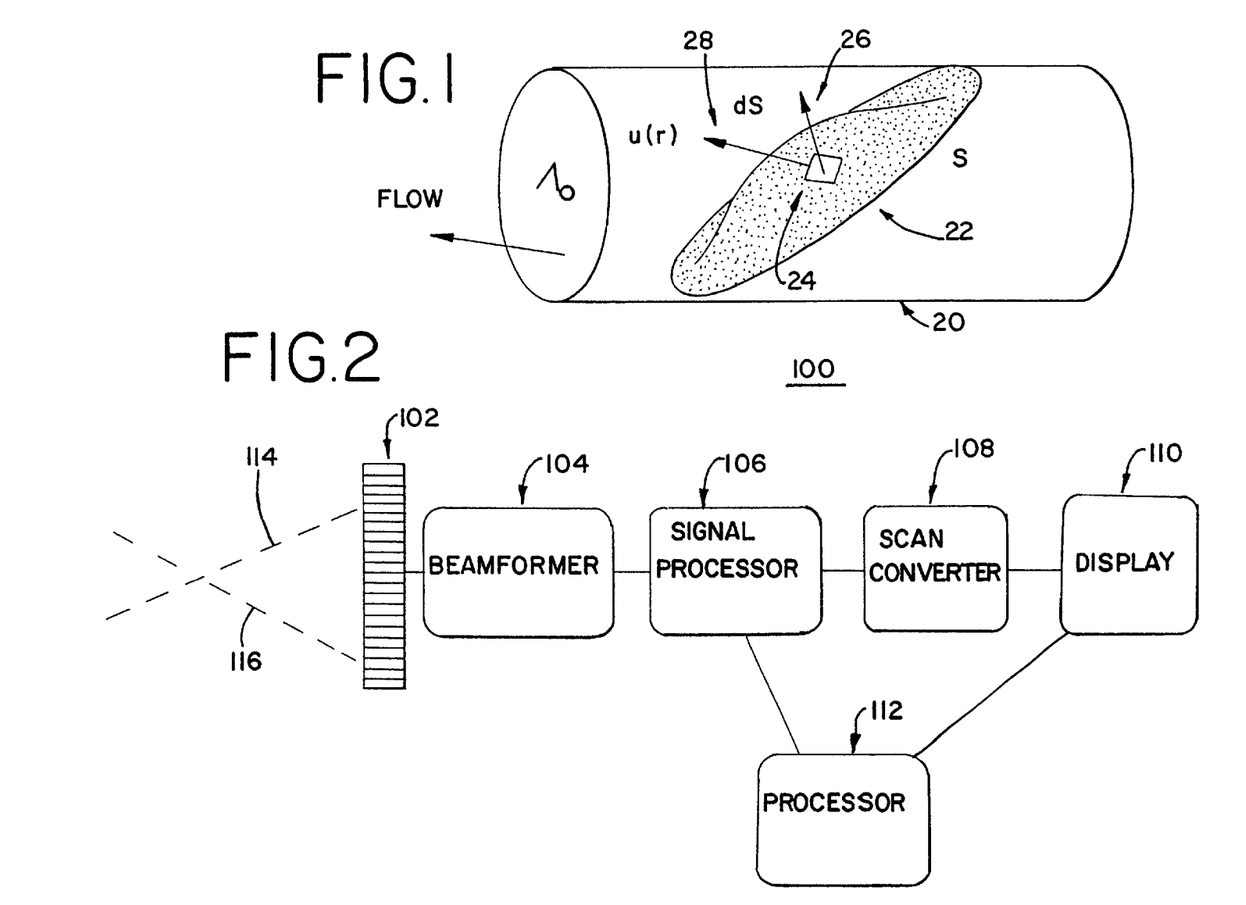
FIG. 1 is a schematic representation of an enclosed structure and a definition of flow.
FIG. 2 is a block diagram of an ultrasound system.

One embodiment of an ultrasound system for calculating volume flow is shown generally at 100 in FIG. 2. The system 100 includes a data path comprising a transducer 102, a beamformer 104, a signal processor (estimator) 106, a scan converter 108 and a display device 110. A processor 112 is connected to the data path, preferably at least to the signal processor 106.

The transducer 102 is any of various transducers, such as a linear or multi-dimensional array of piezoelectric elements. The beamformer 104 is constructed as known in the art. The beamformer 104 may comprise separate transmit and receive beamformers. The beamformer 104 produces excitation signals for each or a subset (i.e. a sub-aperture) of the elements of the transducer 102. The excitation signals are processed, such as by applying a relative delay or amplitude, to focus ultrasonic waveforms along one or more scan lines 114, 116. The scan lines may be at any of various angles relative to the transducer 102 and originate at various locations along the transducer 102. The plane defined by two or more scan lines or any linear combination of transducer elements comprises a scan plane.

The acoustic waveforms are reflected off of structures within a body, including moving fluid within an enclosed structure, as echoes. The echoes are detected by the elements of transducer 102 and provided as voltage signals to the beamformer 104. The beamformer 104 sums the voltage signals and outputs ultrasound data representative of structures along the one or more scan lines.

The signal processor (estimator) 106 is a construction known in the art, such as a Doppler digital signal processor or filtering device for providing Doppler estimates from the representative ultrasound data. The signal processor 106 may also include a parallel B-mode processor or spectral Doppler processor. A clutter filter may also be included. The signal processor 106 estimates the Doppler velocity, energy, and/or variance for each of various points or ranges along each scan line. The estimates and any B-mode information may be stored in a memory, such as a CINE memory.

The estimates, such as Doppler velocity, and/or any B-mode information representing areas in the scan plane or along a scan line are provided to the scan converter 108. The scan converter 108 is a processor or dedicated hardware for formatting the estimates into a Cartesian coordinate system for display.

The display device 110 is a monitor, such as a color monitor. The scan converted ultrasound data representing the scan plane is displayed on the display device 110 as a B-mode intensity, Doppler velocity, Doppler energy, Doppler variance or combination image.

The processor 112 is a digital signal processor or multi-purpose processor for calculating the volume flow from the Doppler velocity estimates. Alternatively, other hardware, such as an accumulator, summer and buffer data path, may calculate the volume flow. The processor 112 obtains information, such as Doppler velocities and Doppler spectrum parameters. The processor 112 also obtains or stores orientation information corresponding to the various scan lines. The information includes values for calculating volume flow as discussed below.

The calculated volume flow quantity, other quantities, waveform and/or waveforms are provided to the display device 110. The calculated information is displayed with or separate from the B-mode or Doppler image. Preferably, the calculated information is displayed in real-time.

The processor 112 may also provide control instructions to various components of the system 100. For example, the processor 112 controls the beamformer 104 to generate acoustic waveforms along scan lines 112, 114 in certain directions and scan formats. Alternatively, a separate processor provides control of the system 100.

The processor 112 or another processor may also coordinate user input. Thus, the user designates a region of interest on a displayed ultrasound image. The region of interest corresponds to pixels associated with the enclosed structure for calculation of volume flow. Alternatively, the region of interest is identified by the system 100 by applying one or more thresholds to the Doppler estimates or B-mode information as discussed below. The identified regions, regardless of the process of identification, are stored in the processor 112, another processor or a memory separate from the processor 112. Alternatively, the user configures the scan plane and associated image to be associated with only the region of interest.

B. Volume Flow Determination

Figure 3A:
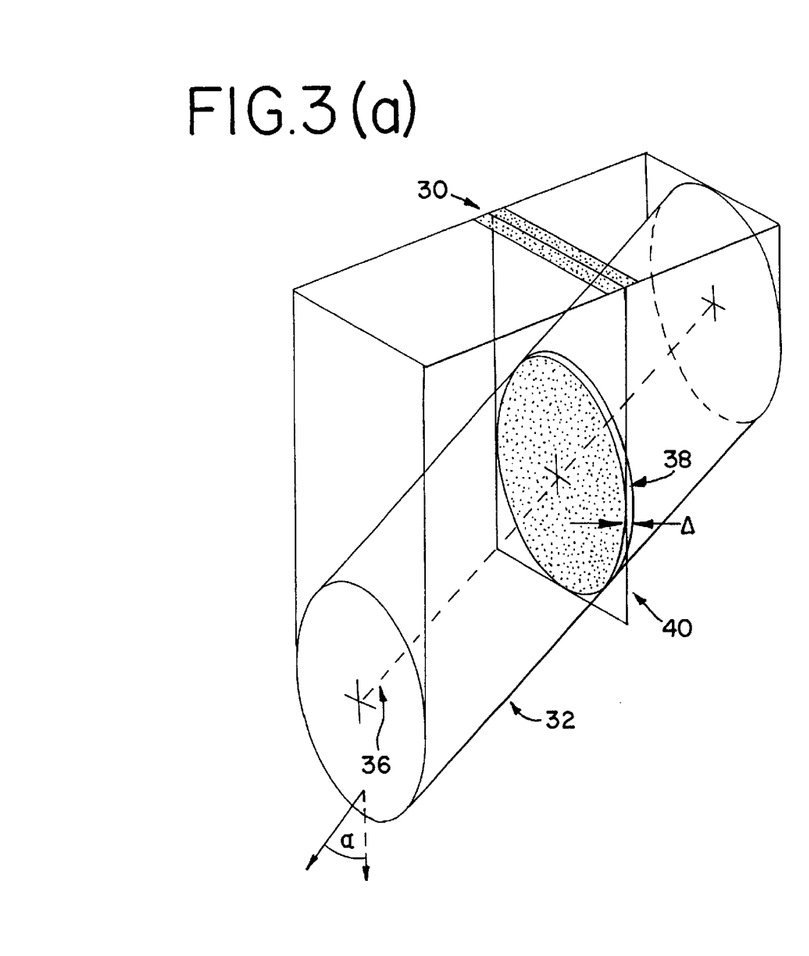
FIGS. 3(a) and 3(b) are schematic perspective representations of relationships between a scan plane and scan lines, respectively, and an enclosed structure.

Using one of the systems described above or another ultrasound system, the volume flow is determined. Referring to FIG. 3(*a*), a portion of the above described method for determining volume flow is graphically represented. A transducer 30 is positioned so that the azimuthal axis is perpendicular to an axis 36 of an enclosed structure 32, such as a vessel. For this arrangement, the instantaneous volume flow is given by:

$$Q = \frac{c}{2f_c \Delta \sigma K} M^1 \tan\alpha \qquad (2)$$

where c is the speed of sound, $f_c$ is the center frequency, $\Delta$ is the thickness of the intersection 38, $\sigma$ is the density of moving scatterers, K includes a scattering coefficient and the path attenuation effects, $M^1$ is the first moment of the Doppler spectrum and $\Delta$ is the Doppler angle (i.e. the angle between the vessel axis 36 and an intersection 38 or a scan plane 40). $M^1$ may be measured; $f_c$ is known or determined from the transmission of the ultrasonic waveform for measuring $M^1$; and $\sigma$, K, $\Delta$ and $\alpha$ are determined from other measurements. The discussion below details obtaining information for these variables.

1. Angle of Flow($\alpha$)

One of multiple techniques determine the angle of flow or Doppler angle $\alpha$. For example, the angle is manually determined. A user may place calipers or other markers to designate the axis 36 on a B-mode, Doppler or other image associated with a scan plane. The angle is calculated from the axis designation and the scan plane position.

In a preferred example, the angle is determined automatically from measurements.

Automatic determination may be more accurate than manual determination. For automatic determination, the user places the transducer 102 on a patient's skin and images an enclosed structure. Preferably, a Doppler mode is used for imaging but other modes, such as B-mode, may be used.

Figure 3B:
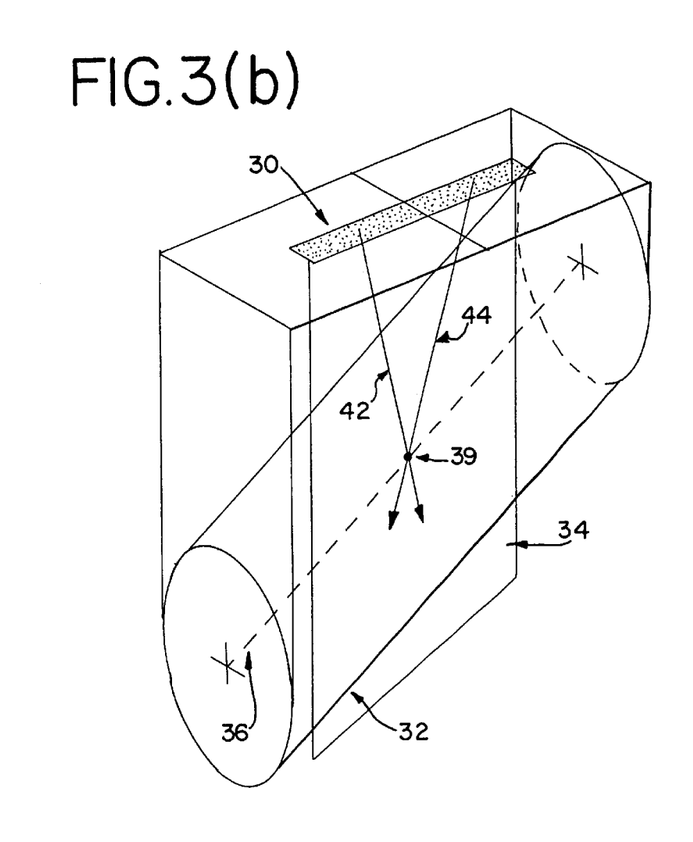
Figure 5:
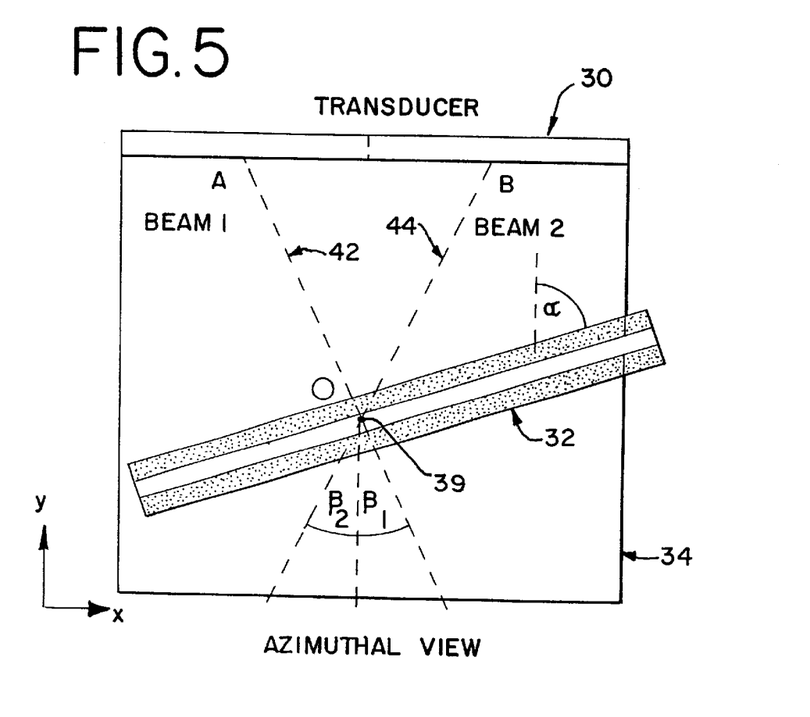
FIG. 5 is a schematic side view representation of a relationship between two scan lines and an enclosed structure.

Referring to FIGS. 3(*b*) and 5, a method of one embodiment for automatically determining the angle or direction of volume flow is graphically represented. The transducer 30 is oriented to image an enclosed structure 32. A B-mode, Doppler or other image is displayed to the user. Preferably, the user maximizes the longitudinal cross section of the displayed enclosed structure 32. By positioning the transducer 30, the user orients a scan plane 34 associated with the displayed image to be generally parallel with an axis 36 of the enclosed structure 32. Preferably, the scan plane 34 intersects the axis 36. For curving enclosed structures 32, the longitudinal cross-section is maximized for the relevant section (ie. near the desired measurement position).

After positioning the transducer 30, the user selects an area 39 within the enclosed structure 32. Preferably, the user places a marker or cursor on the image. Other techniques for selecting the area 38 may be used, such as automatic system selection, such as based on thresholds. After placing the marker, the user activates transmissions of ultrasonic waves for flow angle determination associated with the volume flow calculation. For example, the user depresses a button on a keyboard or touch screen.

In response to activation, the system 100 (FIG. 2) determines the flow angle or angle representing the direction of flow within the enclosed structure 32. Echo data along at least two scan lines 42 and 44 and associated with the area 39 (ie. the range or ranges along each scan line 42 and 44 throughout the enclosed structure 32) is obtained.

The scan lines 42 and 44 are at different angles, $\beta_1$ and $\beta_2$, from the face of the transducer 30 (see FIG. 5). To provide the different angles, the transducer 30 is divided into subapertures A and B. More subapertures may be used. The subapertures may overlap (i.e. use some or all of the same transducer elements).

Using Doppler velocity processing, Doppler velocities (ie. mean velocities) $v_1$ and $v_2$ of the echo data at the area 39 along each scan line 42 and 44 are measured. In alternative embodiments, the mean velocities are calculated using autocorrelation estimation, fast-Fourier transform or cross correlation algorithms.

The Doppler velocities and scan line angles determine the flow angle. For example, simultaneous pulse-chasing is used. This multiple pulse chasing technique is disclosed in U.S. Pat. No. 5,522,393. One ultrasonic wave is transmitted from one of the subapertures A or B or another aperture. Reception processing is performed substantially simultaneously for echoes associated with each scan line 42 and 44 (i.e. subapertures A and B are used to receive echoes at the same time). The Doppler velocities of moving scatterers at the area 39 are equated as represented by:

$$\frac{v_1}{\cos(\alpha + \beta_1)} = \frac{2v_2}{\cos(\alpha + \beta_1) + \cos(\alpha + \beta_2)} \qquad (3)$$

Solving for the flow angle, $\alpha$, equation (3) becomes:

$$\tan\alpha = \frac{\mu\cos\beta_1 - \cos\beta_2}{\mu\sin\beta_1 + \sin\beta_2} \qquad (4)$$

where $$\mu = \frac{2v_2}{v_1} - 1 \qquad (5)$$

The flow angle is determined by measuring the Doppler velocities along at least the scan lines 42 and 44 using equations (4) and (5). The scan lines are associated with known angles relative to the transducer 30. The Doppler velocities may be measured and the flow angle determined by multiple acquisitions and averaged.

In another example, sequential firing is used to determine the flow angle. The subapertures, such as subapertures A and B, are each used to sequentially transmit ultrasound waves and receive echoes. For example, transmission and reception events associated with each subaperture are interleaved. The Doppler velocities are equated as represented by:

$$\frac{v_1}{\cos(\alpha + \beta_1)} = \frac{v_2}{\cos(\alpha - \beta_2)} \qquad (6)$$

Solving for the flow angle, equation (6) becomes:

$$\tan\alpha = \frac{v\cos\beta_1 - \cos\beta_2}{v\sin\beta_1 + \sin\beta_2} \qquad (7)$$

where $$v = \frac{v_2}{v_1} \qquad (8)$$

The flow angle is determined by measuring the Doppler velocities along at least the scan lines 42 and 44 using equations (7) and (8). The Doppler velocities may be measured or the flow angle determined multiple times and averaged (e.g. measurements taken over a period of time, such as a fraction of a second, one or more seconds, or one or more heart cycles).

As yet another alternative, a plurality of ultrasound beams are transmitted substantially simultaneously. A method and system for such transmissions is described in U.S. Pat. No. 5, 675,554. The echo signals are received substantially simultaneously along a plurality of scan lines associated with the transmitted beams.

Simultaneous pulse-chasing May be substantially faster for determining volume flow than sequential firing. Only one transmit event is used for simultaneous pulse-chasing as compared to one transmit event for each scan line for sequential firing. Simultaneous pulse-chasing is more likely to avoid misregistration or other problems associated with movement as a function of time.

2. Density of Scatterers and Scatter/Coefficients/Path Attenuation Effects ($\sigma$ and K)

Figure 4A:
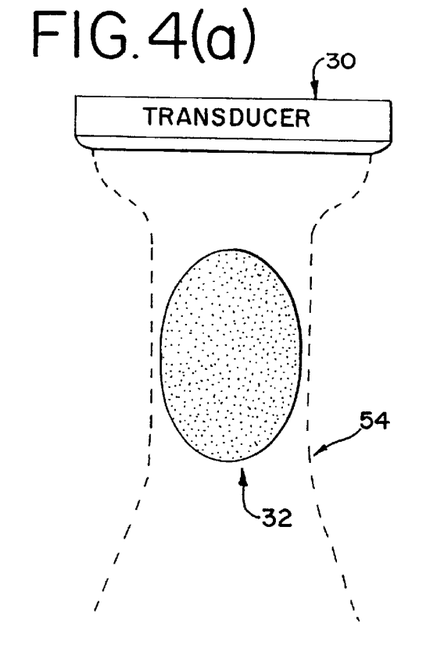
FIGS. 4(a) and 4(b) are schematic representations of two ultrasound beams with different beams widths interrogating a cross-sectional area.
Figure 4B:
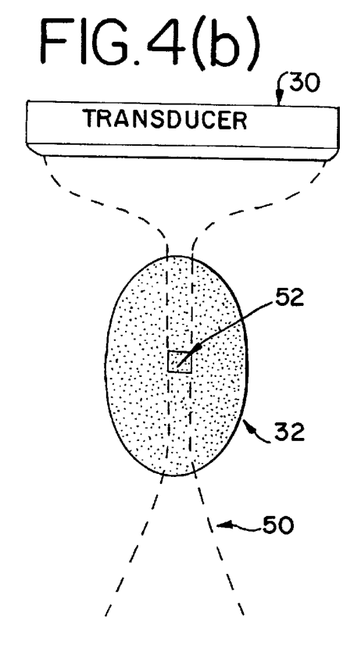

$\sigma$ and K are determined from at least one transmission associated with a different transducer position than the position for determining the flow angle. Referring to FIGS. 3(a), 4(a) and 4(b), the transducer 30 is rotated substantially 90 degrees. The scan plane 40 is substantially perpendicular to the scan plane 34 used for determining the flow angle.

For rotation of the transducer 30, the cross hair of the shaded region (intersection 38) in FIG. 3(a) preferably corresponds to the area 39 of FIG. 3(b). The amount of compression applied by the transducer 30 for both longitudinal and transversal views is preferably the same. To provide similar compression, the user places a cursor to designate a particular point in the imaged structure, such as the center or a near-field portion of the enclosed structure 32. The distances from the transducer 30 to the cursors are kept constant throughout continued imaging, such as between rotations of the transducer 30.

The transducer 30 is positioned transverse to the enclosed structure 32 as discussed above, but the width of the area displayed for the enclosed structure 32 is minimized on a displayed image. Minimization may result in a rotation of less than 90 degrees, and the term substantially perpendicular covers both minimization or rotation close to 90 degrees, without minimization. For minimization, the width of the displayed area of the enclosed structure 32 is minimized by the user or the system 100 (FIG. 2). An automated calculation of area based on border detection may be displayed or used by the system 100 to aid minimization or maximization as discussed above.

After minimization or rotation of the transducer 30, the user designates the enclosed structure 32 as discussed above. For example, the user designates an area, $A_c$, completely within the enclosed structure 32. After designation, the user activates determination of volume flow.

In response to the activation, the system 100 (FIG. 2) calibrates for $\sigma$ and K. As shown in FIG. 4(b), a beam 50 with a known width and spatial extent is transmitted, and corresponding echoes are received. The area of beam 50 is not necessarily small, but is preferably enclosed by the enclosed structure 32. The echoes are processed to isolate information associated with the area, $A_c$, 52 (e.g. one range gate). A zeroth moment, $M^0_c$, of a Doppler spectrum associated with the isolated echo information (i.e. area 52) is calculated. If the area 52 is completely within the enclosed structure 32, then:

$$A_c = \frac{M^0_c}{\Delta \sigma K} \quad (9)$$

Combining equations (9) and (2), the volume flow is calculated as:

$$Q = \frac{cA_c}{2f_c} \frac{M^1}{M^0_c} \tan\alpha. \quad (10)$$

In summary, $\sigma$ and K are calibrated or accounted for by measuring the zeroth moment (i.e. a Doppler parameter) of the known area 52. This measurement may be obtained over different time intervals to account for vessel and flow plusitility.

3. First Moment Parameter ($M^1$)

After calibration and determination of the flow angle, instantaneous volume flow is calculated by measuring the first moment (i.e. a Doppler parameter). To determine the first moment, the enclosed structure 32 is uniformly insonified. Echo information is received. The first moment is measured from the Doppler spectrum of the echo information associated with a range substantially covering the enclosed structure 32.

As represented by FIG. 4(a), a beam 54 associated with a wide beam profile in the scan plane is transmitted. Preferably, the beam 54 substantially covers the enclosed structure 32. For example, points of the beam profile −6 dB from the peak (the dashed beam boarders) lay outside of the enclosed structure 32. Substantially the entire enclosed structure 32 is uniformly insonified. Preferably, for ranges corresponding to the enclosed structure 32, the beam 54 does not intersect any moving fluids or structures not associated with the enclosed structure 32.

The width and range of the ultrasound beam for uniform insonification is determined as a function of user input or by automatic methods. Either the user designated a width or designates a point in the enclosed structure 32. If the user designates a point, the system 100 (FIG. 2) determines an area for insonification associated with fluid flow. The processor 112 (FIG. 2) applies selection criteria to determine whether there is valid fluid flow data associated with each pixel or sample volume. Doppler or B-mode values only or in combination are used to determine valid fluid flow. For example, if the amplitude of the B-mode signal associated with a pixel is high, a Doppler value for such pixel may not be a reliable indication of fluid flow. A low B-mode value and a high Doppler value indicates fluid flow. If the information corresponds to fluid flow, then the pixel is included in the area to be uniformly insonified. The width is determined from the area.

The profile of the beam 54 is widened using various methods, such that the enclosed structure is uniformly insonified. For example, (1) a sinc apodization function is used to provide a wide rectangular beam profile pattern; (2) the aperture width associated with the beam 54 is appropriately adjusted; (3) low frequencies are used with the beam 54; or (4) the beam 54 is defocused, such as using appropriate delays or moving the focus nearer or beyond the enclosed structure 32. All four methods may be used together, and other methods for providing a wide beam profile may be used.

The Doppler spectrum associated with the echo information is computed. The power returned by scatterers having Doppler shifts between a first frequency $f_d$ and a second frequency, $f_d + df_d$, is represented by the function $P(f_d)df_d$.

$M^0$ and $M^1$, the zeroth and first moments of the Doppler spectrum, are represented by:

$$M^0 = \int P(f_d) df_d, \quad \text{and} \quad (11)$$

$$M^1 = \int f_d P(f_d) df_d, \quad \text{respectively.} \quad (12)$$

Using the first moment associated with the beam 54, the zeroth moment and area associated with the calibration beam 50, and the flow angle, volume flow is calculated.

After determining the instantaneous volume flow as discussed above, the quantity is displayed in real-time to the user or used to generate a waveform of volume flow as a function of time. The instantaneous volume flow calculation may be repeated in real time. The flow angle and calibration information (i.e. $\alpha$, $A_c$ and $M^0_c$) are preferably used for each volume flow calculation during each imaging sequence, but may be measured for each or a subset of all the volume flow calculations. Using the same flow angle and calibration information, the enclosed structure is repetitively uniformly insonified and new first moments are calculated. The new first moments are used to calculate new volume flow quantities. An average of the instantaneous volume flow quantities may also be displayed. Other quantities such as the area, Doppler moments or angle may be displayed.

C. Multi-Dimensional Transducers

Figure 6A:
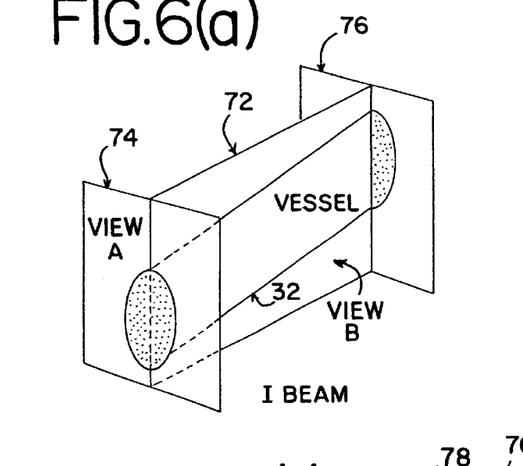
FIGS. 6(a), 6(b) and 6(c) are schematic representations of intersections of a vessel with scan planes associated with I beam, T beam and + beam transducers, respectively.
Figure 6B:
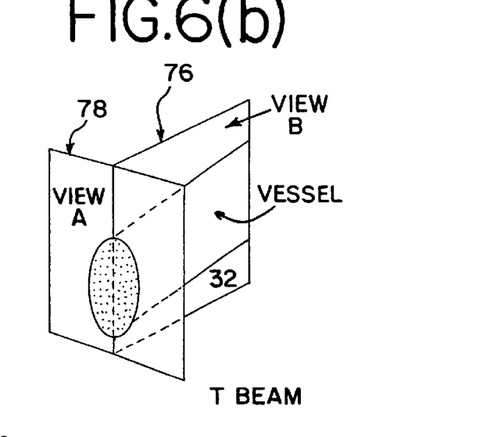
Figure 6C:
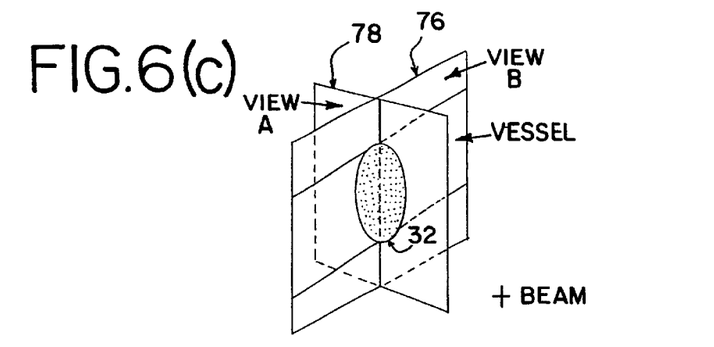

In alternative embodiments, multi-dimensional transducers are used. For example, I beam, T beam, + beam, 1.5 or 2 dimensional transducers are used. These transducers include elements arrayed on a plane (i e. arrayed in two dimensions). For a description of an I beam transducer, see U.S. application Ser. No. 08/916,163, filed Aug. 21, 1997. The I beam transducer generally includes elements in the plane arrayed in an I pattern. As shown in FIG. 6(a), three scan planes 70, 72, and 74 associated with the I pattern may be generated. As shown in FIGS. 6(b) and 6(c), two scan planes 76 and 78 associated with the T and + patterns, respectively, may be generated. Transducers with other element patterns may be used. For 1.5 or 2 dimensional transducers, any of the various scan plane formats or patterns may be generated.

Using multi-dimensional transducers, the user holds the transducer in one position for calculating volume flow. One scan plane, such as scan planes 72 or 76, is used for determining the flow angle as discussed above. For example, the user rotates the multi-dimensional transducer so that the longitudinal view of the enclosed structure 32 associated with one scan plane 72 or 76 is maximized (e.g. view B). Once positioned, another scan plane (e.g. view A), such as one of scan planes 70, 74 or 78, is substantially perpendicular to the scan plane 72 or 76 associated with maximization. Alternatively, the user rotates the multi-dimensional transducer so that the width of the transversal view of the enclosed structure 32 in one scan plane 70, 74 or 78 is minimized (e.g. view B). Without rotating the transducer, the scan plane 70, 74 or 78 associated with view A is used to calibrate and measure the first moment as discussed above. For the I beam transducer, one or both of the scan planes 70 and 74 associated with view A are used to calculate volume flow. If both are used, then the resulting quantities may be averaged or displayed separately.

Using a two-dimensional transducer, the scan planes associated with views A and B may be independently minimized or maximized, respectively. Therefore, the scan plane associated with view A may be at an angle less than 90 degrees to the scan plane associated with view B.

Figure 7:
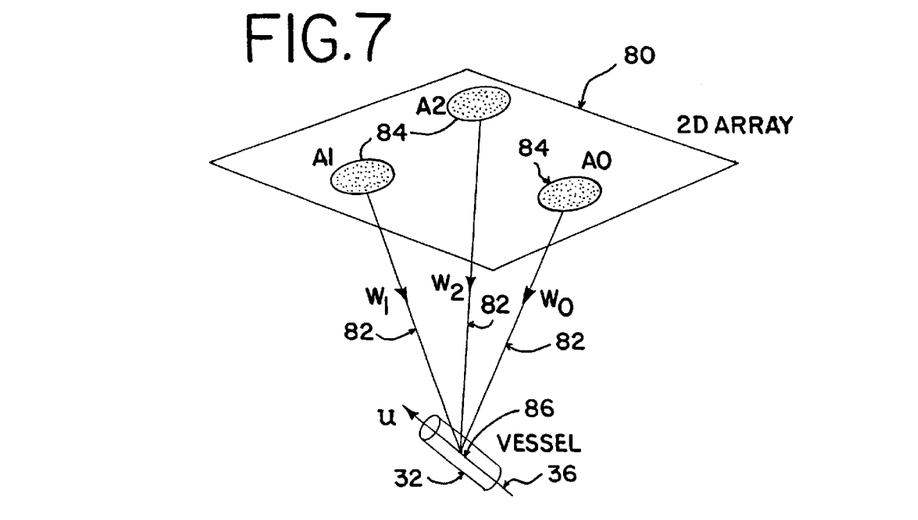
FIG. 7 is a schematic representation of a relationship between a vessel and a two-dimensional transducer array.

Using a multi-dimensional transducer, the volume flow may be calculated without minimization or maximization. Preferably, a two-dimensional transducer 80 is used as shown in FIG. 7. The transducer is positioned to image an arbitrary cross-section of the enclosed structure 32. The multi-dimensional transducers allow measurement of the orientation of the axis 36 in three-dimensions.

The orientation is determined by transmissions along three or more scan lines 82. The three scan lines 82 are associated with different positions or three-dimensional orientations. The scan lines 82 intersect at an volume 86 within the enclosed structure. For example, three subapertures 84 on the two-dimensional transducer 80 are used to generate the ultrasonic waves along the scan lines 82 in response to user designation of the volume 86. The system 100 (FIG. 2) determines appropriate subapertures and scan line orientations in response to the designation of the volume 86. For I beam, T beam and + beam transducers, the transducer is positioned so that volume 86 is located along an intersection of perpendicular scan planes.

Volume flow is calculated as a function of the flow orientation in three-dimensions and uniform insonification of the enclosed structure as discussed above. The flow orientation or angle in three-dimensions is calculated as a function of the orientation of the scan lines 82 and mean velocities associated with each of the scan lines 82. In the case of three scan lines 82, $w_0$, $w_1$, and $w_2$ represent unit vectors defining the orientation of the scan lines 82, and $u$ represents a unit vector defining the orientation of the axis 36. For simultaneous pulse chasing (i.e. transmitting along scan line A0 and receiving along scan lines A0, A1, and A2), the dot product, $h_i$, of $w_i \cdot u$, where $i=0, 1 \ldots N$ (the number of scan lines minus 1) is used to represent the relationship between the scan lines and velocities:

$$\frac{v_0}{h_0} = \frac{2v_1}{h_o + h_1} = \frac{2v_2}{h_0 + h_2} \quad (13)$$

where $v_0$, $v_1$, $v_2$ and are the mean velocities measured along the scan lines 82 for the volume 86. The mean velocities are obtained using either simultaneous or sequential transmissions as discussed above. Defining:

$$\mu_1 = \frac{v_1}{v_0} - 1 \quad \text{(simultaneous transmission)} \quad (14A)$$

$$\mu_1 = \frac{v_1}{v_0} \quad \text{(sequential transmission)} \quad (14B)$$

$$\mu_2 = \frac{v_2}{v_0} - 1 \quad \text{(simultaneous transmission)} \quad (15A)$$

$$\mu_2 = \frac{v_2}{v_0} \quad \text{(sequential transmission)} \quad (15B)$$

$$h = \begin{bmatrix} 1 \\ \mu_1 \\ \mu_2 \end{bmatrix} \quad \text{and} \quad (16)$$

$$A = [w_0 w_1 w_2], \quad (17)$$

the enclosed structure 32 orientation is given by:

$$u = \frac{q}{|q|} \quad (18)$$

where, $q=A$

Using equations (18) and (19), the vessel orientation u is determined. The Doppler angle or flow angle is given by:

$$\cos\alpha = u \cdot w \quad (20)$$

where w is the orientation of a scan line, such as one of scan lines 82, a different scan line or a combination of scan lines (ie. average). Based on the Doppler angle and at least one uniform insonification of the enclosed structure, the volume flow is determined.

D. Alternate Volume Flow Determination

Using the system 100 (FIG. 2) and many of the techniques discussed above, volume flow as defined in FIG. 1 may be calculated in an alternate method. The method described above includes determining an angle of the enclosed structure 32 associated with a longitudinal image and then determining volume flow from data associated with a cross-sectional image. In the alternate method, calibration and normalization steps are first performed and are associated with a cross-sectional image, and then volume flow is calculated from data associated with a longitudinal image.

Figure 8A:
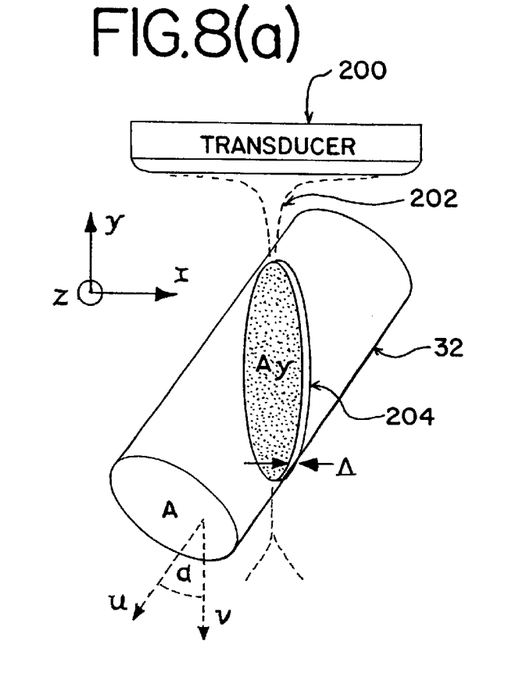
FIGS. 8(a) and 8(b) are schematic representations of relationships between transmitted and received beams and an enclosed structure.
Figure 8B:
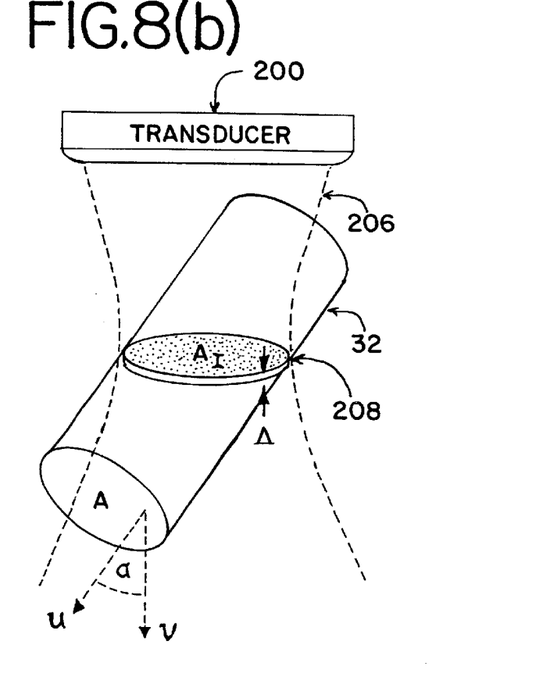

Referring to FIG. 8, volume flow is calculated from data associated with the longitudinal image using axial insonification (FIG. 8(*a*)), azimuthal insonification (FIG. 8(*b*)) or a combination thereof. Uniform insonification is preferably used for both axial and azimuthal insonification. For axial insonification, a linear transducer 200 transmits a beam 202 with a narrow beam width and receives echo signals. The echo signals are associated with a range gate size large enough to include the entire enclosed structure 32. Data representing the area 204, $A_y$, with a width $\Delta$ is obtained. For azimuthal insonification, the linear transducer 200 transmits a beam 206 with a wide beam width substantially covering the enclosed structure 32. The echo signals are associated with a small range gate, such as $\Delta$. Data representing the area 208, $A_x$, is obtained.

The volume flow is determined from the axial and azimuthal insonification data from the following equations:

$$Q_y = \frac{c}{2f_c \Delta \sigma K} M^1 \tan\alpha \quad (21)$$

$$Q_x = \frac{c}{2f_c \Delta \sigma K} M^1, \quad (22)$$

respectively. Equation 22 is independent of the flow angle, $\alpha$. For equation 21, the flow angle is determined as discussed above. $\sigma$ and K are determined as discussed below. All other quantities in equations 21 and 22 are known as discussed above.

If the enclosed structure 32 is or is close to parallel to the linear transducer 200, the axial volume flow calculation (i.e. equation 21) provides accurate estimations, and the azimuthal volume flow calculation (i.e. equation 22) provides less accurate estimations. Conversely, if the enclosed structure 32 is or is close to perpendicular to the linear transducer 200, the azimuthal volume flow calculation provides accurate estimations, and the axial volume flow calculation provides less accurate estimations. Less accurate estimations include values associated with noise. Preferably, the system 100 automatically selects the insonification technique associated with the highest accuracy estimates. For example, the multiple sub-aperture simultaneous pulse chasing method or the sequential firing method described above is used to determine the orientation of the enclosed structure 32. If the enclosed structure 32 is oriented closer to parallel than perpendicular to the transducer 100, axial insonification is used. If the enclosed structure 32 is oriented closer to perpendicular than parallel to the transducer 100, azimuthal insonification is used. Alternatively, the user manually tilts the transducer 100 to avoid parallel or perpendicular imaging, such as rotating the transducer 100 around the azimuthal axis while imaging the cross-section of the enclosed structure 32.

Figure 9:
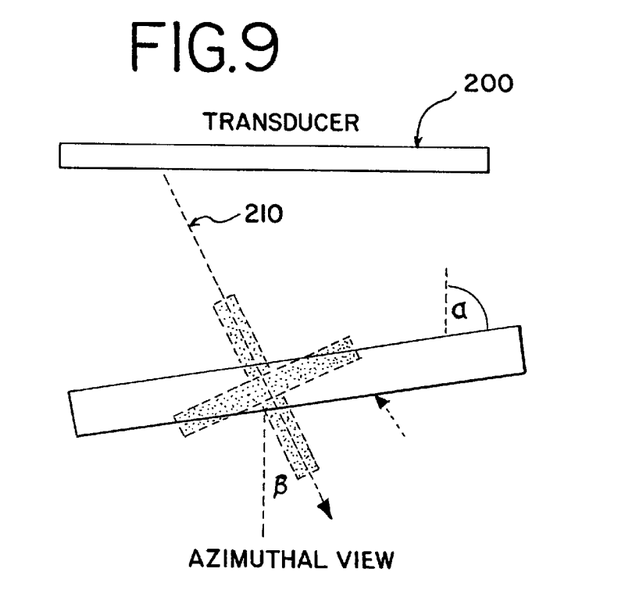
FIG. 9 is a schematic representation of a relationship between a scan line and an enclosed structure.

To further improve accuracy of the volume flow estimates, the system 100 makes multiple measurements. Referring to FIG. 9, the multiple measurements are preferably associated with different angles of insonification. For example, the beams are transmitted along scan lines 210 at different angles, $\beta$, to the line normal to the transducer 200. For azimuthal volume flow estimation, equation 22 is used. For axial volume flow estimation, equation 21 becomes:

$$Q_y = \frac{c}{2f_c \Delta \sigma K} M^1 \tan(\alpha + \beta) \quad (23)$$

The angle $\beta$ is changed and a corresponding number of estimates are obtained. Simultaneous pulse chasing may be used for measuring the first moment at different angles $\beta$. The estimates are combined to determine volume flow. For example, the estimates are averaged or weighted and averaged. Furthermore, estimates associated with axial estimation may be combined with estimates associated with azimuthal estimation.

Figure 10A:
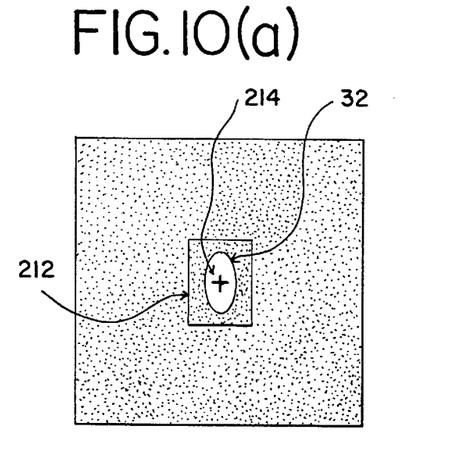
FIGS. 10(a) through 10(d) represent images associated with determining volume flow and FIG. 10(e) represents a display of volume flow as a waveform.

Before measuring the first moment as discussed above and for improved accuracy, a normalization factor, $\kappa$, is determined. The transducer is first positioned to image the cross-section of the enclosed structure 32 (i.e. transverse to the enclosed structure 32) as shown in FIGS. 4 and 10(*a*). Preferably, the user positions a region of interest or box 212 around the enclosed structure. The box 212 is preferably sized to be as small as possible and include all of the enclosed structure 32. In alternative embodiments, the region of interest is determined automatically. The user or the system 100 also may place a icon or cursor 214 at the center of the enclosed structure 32 for guiding the beams as discussed below.

The normalization factor, $\kappa$, compensates for axial and azimuthal insonification where the elevation thickness of the beam pattern does not completely cover the enclosed structure 32. The elevation thickness is represented as the portion of area 204 or 208 along the z dimension in FIG. 8. Referring to FIG. 4(*a*), the beam 54 with a width encompassing the enclosed structure 32 is generated. The range gate size preferably also encompasses the enclosed structure 32. The first moment, $M^1_w$, of the wide beam 54 is calculated. Referring to FIG. 4(*b*), the beam 50 with an azimuthal width the same as the elevation thickness throughout the enclosed structure 32 is generated. The range gate size preferably also encompasses the enclosed structure 32. The first moment, $M^1_n$, of the narrow beam 50 is calculated. Assuming that the flow through the enclosed structure 32 represented by FIG. 4 is the same as the flow through $A_y$ or $A_x$ of FIG. 8, the normalization factor is:

$$\kappa = \frac{M^1_w}{M^1_n} \quad (24)$$

Using the normalization factor, equations 21 and 22 are represented as:

$$Q_y = \frac{\kappa c}{2f_c \Delta \sigma K} M^1 \tan\alpha \quad (25)$$

and $$Q_x = \frac{\kappa c}{2f_c \Delta \sigma K} M^1, \quad (26)$$

respectively.

While the transducer is in the cross-sectional image position, σ and κ are also calibrated. Referring to FIG. 4(b), the beam 50 with a known width is transmitted, and corresponding echoes are received. The echoes are processed to isolate information associated with the area 52, $A_c$, (e.g. one range gate). The zeroth moment, $M^0{}_c$, of a Doppler spectrum associated with area 52 is calculated. If the area 52 is completely within the enclosed structure 32, then:

$$A_c = \frac{M_c^0}{\Delta_c \sigma K} \quad (27)$$

where $\Delta_c$ is the elevation thickness associated with the beam 50. The zeroth moment may be calculated from echoes associated with the narrow beam used for determining the normalization factor, but with a different range gate size.

Using equations 25, 26 and 27:

$$Q = \frac{\kappa c A_c \Delta_c}{2f_c \Delta} \frac{M^1}{M_c^0} \tan \alpha \quad (28)$$

$$Q = \frac{\kappa c A_c \Delta_c}{2f_c \Delta} \frac{M^1}{M_c^0}. \quad (29)$$

The quantities in equations 28 and 29 are known or measurable. After measuring quantities associated with the normalization factor and σ and K, measurements associated with the axial and/or azimuthal insonification are made and volume flow is estimated.

For estimating volume flow with axial or azimuthal insonification, the transducer 200 is rotated approximately 90° around the y-axis (see FIG. 8). Referring to FIG. 10, the image associated with the transducer position changes from the cross-section shown in FIG. 10(a) to the longitudinal view shown in FIG. 10(b). Volume flow is then estimated as discussed above.

Figure 10B:
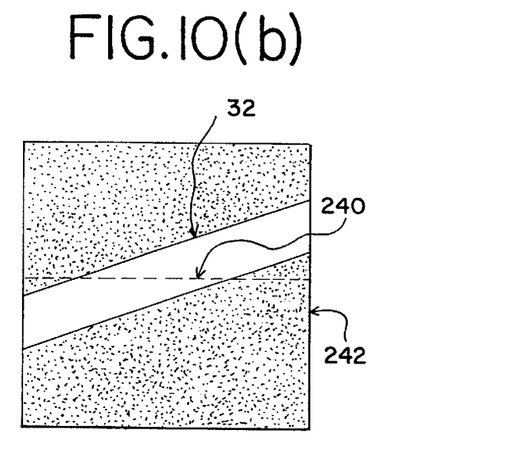
Figure 10C:
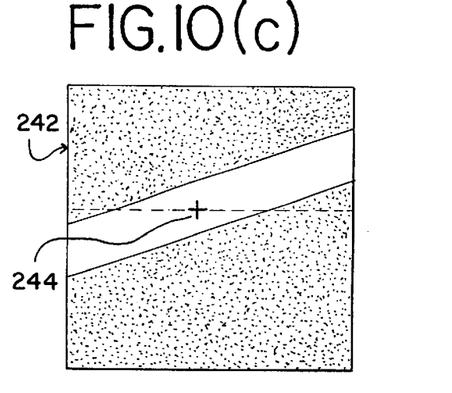
Figure 10D:
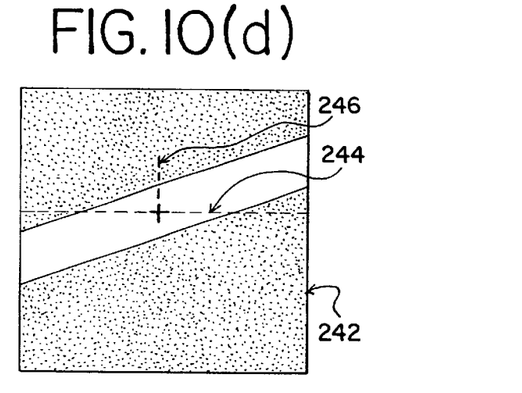

In one embodiment, the user presses a button or indicates that the transducer 200 has been rotated. A horizontal line 240 is placed in the image 242 by the system 100 and is at the same depth as the cursor 214. The user maximizes the size of the enclosed structure 32 by moving the transducer 200 in the elevation dimension. The user then presses a button or indicates completion of the placement of the transducer 200. The system 100 generates a cursor 244 on the image 242. The user positions the cursor 244 approximately at the center of the enclosed structure 32 along the horizontal line 240. Completion of placement of the cursor 244 is indicated by the user. The system 100 then determines the angle of flow at the cursor 244 and determines which insonification technique, axial or azimuthal, may provide the most accurate estimates of volume flow. The system 100 generates a vertical line 246 for axial insonification or highlights the horizontal line 244 for azimuthal insonification. The user then sizes the vertical or horizontal line 244 or 246 to extend just beyond the enclosed structure 32 and presses a button to begin axial or azimuthal insonification. Based on the vertical or horizontal line 244 or 246, the system 100 generates one or more uniform transmit beams for axial or azimuthal insonification, and estimates volume flow.

Instantaneous volume flow through many enclosed structures 32 varies in a periodic fashion with the cardiac cycle. Furthermore, the cross-section dimensions of the enclosed structure 32 may change throughout the cardiac cycle. The normalization factor, σ, and K estimated at one instant in time may not be suitable for estimation of volume flow at all times throughout the cardiac cycle. Preferably, each of these factors is determined at a number of different times during a cardiac cycle. Each different factor and corresponding estimates of volume flow are registered with a triggered time stamp, such as from an ECG trigger. Alternatively, a waveform of $M^1{}_n$, $M^1{}_w$, $M^1$, a combination thereof or other measured parameters that vary as a function of the cardiac cycle is used to designate different times throughout the cardiac cycle. Volume flow is estimated using the normalization factor associated with the same or similar portions of the cardiac cycle.

Figure 10E:
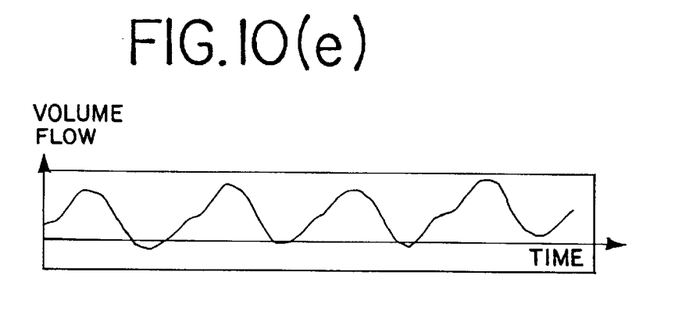

A waveform representing volume flow is preferably generated as shown in FIG. 10(e). Other parameters, such as stroke volume, heart rate, vessel area, Doppler moments and average volume flow, are also preferably displayed.

While the invention has been described above by reference to various embodiments, it will be understood that different changes and modifications can be made without departing from the scope of the invention. For example, dedicated hardware or multi-processors may be used for any of the various calculations. Additionally, differing formulas may be used to obtain the same or similar quantities.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. A method for measuring flow of fluid in an enclosed structure with an ultrasound system, the method comprising the steps of:
   (a) uniformly insonifying a first area of the enclosed structure;
   (b) measuring a first parameter of a Doppler spectrum responsive to step (a);
   (c) obtaining an angle associated with a direction of flow in the enclosed structure; and
   (d) determining volume flow as a function of the first parameter and the angle.

2. The method of claim 1 further comprising:
   (e) insonifying a second area within the enclosed structure, the second area less than the first area;
   (f) measuring a second parameter of a second Doppler spectrum responsive to step (e);
   wherein step (d) comprises determining the volume flow as a function of the first parameter, the second parameter and the angle.

3. The method of claim 2 wherein:
   the first parameter comprises a first moment;
   the second parameter comprises a zeroth moment; and
   step (d) comprises determining the volume flow as a function of the first and second parameters, a center frequency associated with step (a), the second area and the angle.

4. The method of claim 1 wherein step (c) comprises (c1) measuring a first velocity associated with a second area and a first scan line at a first scan angle;
   (c2) measuring a second velocity associated with the second area and a second scan line at a second scan angle; and (c3) determining the angle associated with the direction of flow in the enclosed structure as a function of the first and second velocities and first and second scan angles.

5. The method of claim 4 wherein step (a) is associated with a first scan plane and step (c) is associated with a second scan plane substantially perpendicular to the first scan plane.

6. The method of claim 5 further comprising:
   (e) selecting the second area; and
   wherein step (c) is performed before step (a).

7. The method of claim 6 further comprising:
   (f) orienting a transducer associated with the first scan plane;
   (g) repeating steps (a), (b) and (d) in the orientation of step (f); and
   (h) repetitively displaying volume flow in response to step (g).

8. The method of claim 5 further comprising (e) rotating a transducer between steps (c) and (a).

9. The method of claim 5 further comprising (e) using a multi-dimensional transducer.

10. The method of claim 1 further comprising (e) using a multi-dimensional transducer;
    wherein the first area comprises a first volume
    wherein step (c) comprises
        (c1) measuring a first velocity associated with a second volume and a first scan line at a first scan angle;
        (c2) measuring a second velocity associated with the second volume and a second scan line at a second scan angle;
        (c3) measuring a third velocity associated with the second volume and a third scan line at a third scan angle; and
        (c4) determining the angle associated with the direction of flow in the enclosed structure as a function of the first, second and third velocities and first, second and third scan angles.

11. The method of claim 1 wherein step (b) is responsive to a simultaneous pulse chasing transmission.

12. The method of claim 1 wherein step (a) comprises axial insonifying.

13. The method of claim 1 wherein step (a) comprises azimuthal insonifying.

14. The method of claim 1 further comprising:
    (e) obtaining a first first moment associated with a wide transmit beam;
    (f) obtaining a second first moment associated with a narrow transmit beam; and
    (g) normalizing the volume flow as a function of the first and second first moments.

15. The method of claim 1 further comprising:
    (e) imaging a cross-section of the enclosed structure;
    (f) determining a value representing a density of scatterers, a scattering coefficient, and path attenuation effects;
    (g) imaging a longitudinal section of the enclosed structure; and
    (h) performing steps (a), (b) and (c) associated with the longitudinal section.

16. An ultrasound system for measuring flow of fluid in an enclosed structure comprising:
    a transducer;
    a beamformer for uniformly insonifying a first area of the enclosed structure
    an estimator for measuring a first parameter of a Doppler spectrum responsive to the uniform insonification; and
    a processor for determining volume flow as a function of the first parameter and an angle associated with a direction of flow in the enclosed structure.

17. A method for measuring flow of fluid in an enclosed structure with an ultrasound system, the method comprising the steps of:
    (a) measuring a first parameter of a first Doppler spectrum;
    (b) measuring a first velocity associated with a first area and a first scan line at a first angle;
    (c) measuring a second velocity associated with the first area and a second scan line at a second angle;
    (d) determining a flow angle associated with flow in the enclosed structure as a function of the first and second velocities and first and second angles; and
    (e) determining volume flow of the enclosed structure as a function of the first parameter and the flow angle.

18. The method of claim 17 wherein step (a) comprises:
    (a1) uniformly insonifying a second area of the enclosed structure; and
    (a2) measuring the first parameter as a first moment of the Doppler spectrum responsive to step (a1).

19. The method of claim 18 further comprising:
    (f) insonifying a third area within the enclosed structure, the third area less than the second area;
    (g) measuring a zeroth moment of a second Doppler spectrum responsive to step (f);
    wherein step (e) comprises determining the volume flow as a function of the first moment, the zeroth moment, a center frequency associated with step (a), the third area and the flow angle.

20. The method of claim 17 wherein step (a) is associated with a first scan plane and steps (b) and (c) are associated with a second scan plane substantially perpendicular to the first scan plane.

21. The method of claim 20 further comprising (f) rotating a transducer between (1) steps (b) and (c) and (2) step (a).

22. The method of claim 20 further comprising (f) using a multi-dimensional transducer.

23. The method of claim 17 wherein the first area comprises a first volume and further comprising:
    (f) using a multi-dimensional transducer; and
    (g) measuring a third velocity associated with the first volume and a third scan line at a third scan angle;
    wherein step (d) comprises determining the flow angle as a function of the first, second and third velocities and first, second and third scan angles.

24. The method of claim 17 wherein steps (b) and (c) are associated with a simultaneous pulse-chasing reception.

25. The method of claim 17 wherein steps (b) and (c) are associated with separate receive events.

26. An ultrasound system for measuring flow of fluid in an enclosed structure comprising:
    a transducer;
    an estimator for measuring (1) a first parameter of a Doppler spectrum, (2) a first velocity associated with a first area and a first scan line at a first angle, and (3) a second velocity associated with the first area and a second scan line at a second angle; and
    a processor for determining (1) a flow angle associated with flow in the enclosed structure as a function of the first and second velocities and the first and second angles and (2) volume flow as a function of the first parameter and the flow angle.

27. A method for measuring flow of fluid in an enclosed structure with an ultrasound system, the method comprising the steps of:

(a) uniformly insonifying a first area of the enclosed structure in a first scan plane;

(b) measuring a first moment of a first Doppler spectrum responsive to step (a);

(c) measuring a first velocity associated with a first area and a first scan line at a first angle in a second scan plane, the second scan plane substantially perpendicular to the first scan plane;

(d) measuring a second velocity associated with the first area and a second scan line at a second angle in the second scan plane, (e) determining a flow angle associated with flow in the enclosed structure as a function of the first and second velocities and first and second angles; and (f) determining volume flow as a function of the first moment and the flow angle.

28. The method of claim 27 further comprising:

(g) insonifying a third area within the enclosed structure, the third area less than the first area;

(h) measuring a zeroth moment of a second Doppler spectrum responsive to step (g);

wherein step (f) comprises determining the volume flow as a function of the first moment, the zeroth moment, a center frequency associated with step (a), the third area and the flow angle.

29. The method of claim 27 wherein step (a) is associated with a first scan plane and steps (c) and (d) are associated with a second scan plane substantially perpendicular to the first scan plane.

30. An ultrasonic method for measuring flow of fluid in an enclosed structure with an ultrasound system, the method comprising the steps of:

(a) determining scatterer calibration values associated with a transversal cross-section of the enclosed structure;

(b) uniformly insonifying in an azimuthal dimension with a linear transducer the enclosed structure associated with a longitudinal cross-section; and (c) determining volume flow as a function of the scatterer calibration values and the uniform insonification.

31. The method of claim 30 further comprising (d) determining a normalization factor wherein volume flow is determined as a function of the normalization factor.

* * * * *

UNITED STATES PATENT AND TRADEMARK OFFICE
CERTIFICATE OF CORRECTION

PATENT NO. : 6,293,914 B1
DATED : September 25, 2001
INVENTOR(S) : Thilaka S. Sumanaweera et al.

It is certified that error appears in the above-identified patent and that said Letters Patent is hereby corrected as shown below:

Column 5,
Line 23, delete "Δ" and substitute -- α -- in its place.

Column 7,
Line 9, delete "5, 675,554." and substitute -- 5,675,554. -- in its place.
Line 12, delete "May" and substitute -- may -- in its place.
Line 19, delete "Scatter/" and substitute -- Scatterer/ -- in its place.

Column 10,
Line 9, delete "at an" and substitute -- at a -- in its place.
Line 64, delete "g=A" and substitute -- $q = A[A^T A]^{-1} h$ -- in its place.

Signed and Sealed this

Tenth Day of December, 2002

JAMES E. ROGAN
*Director of the United States Patent and Trademark Office*